United States Patent [19]

Zeibig

[11] 4,225,981
[45] Oct. 7, 1980

[54] ENDO PROTHESIS WITH A METAL-CERAMIC UNION

[75] Inventor: Anton Zeibig, Ottensoos, Fed. Rep. of Germany

[73] Assignee: Rosenthal Technik AG, Bavaria, Fed. Rep. of Germany

[21] Appl. No.: 935,804

[22] Filed: Aug. 22, 1978

[30] Foreign Application Priority Data

Sep. 19, 1977 [DE] Fed. Rep. of Germany ....... 2742098

[51] Int. Cl.³ ............................................. A61F 1/03
[52] U.S. Cl. ..................................... 3/1.913; 29/447; 85/46; 128/92 CA; 151/22; 403/343
[58] Field of Search ....................... 3/1.9, 1.91, 1.911, 3/1.912, 1.913; 128/92 C, 92 CA; 403/343, 342; 85/46, 48; 151/22; 29/428, 447

[56] References Cited

U.S. PATENT DOCUMENTS

| 1,780,826 | 11/1930 | Kuhn | 403/343 |
| 1,817,808 | 8/1931 | Eaton | 29/447 |
| 2,367,213 | 1/1945 | Harding | 151/22 X |
| 3,258,284 | 6/1966 | Phipps | 85/46 X |
| 3,707,107 | 12/1972 | Bieri | 85/46 X |
| 3,987,499 | 10/1976 | Scharbach et al. | 3/1.913 X |
| 4,040,756 | 8/1977 | Donegan | 403/343 X |

FOREIGN PATENT DOCUMENTS

| 757828 | 5/1967 | Canada | 85/46 |
| 2318396 | 10/1974 | Fed. Rep. of Germany | 3/1.913 |
| 2548077 | 5/1977 | Fed. Rep. of Germany | 3/1.913 |

Primary Examiner—Clifford D. Crowder
Attorney, Agent, or Firm—Ostrolenk, Faber, Gerb & Soffen

[57] ABSTRACT

In a bone joint endoprosthesis, the spigot of the metal shank is externally threaded to mate with a thread inside the ceramic head of the prosthesis; the thread on the spigot has greater depth in the radial direction, with flat sides, and the depth of the thread in the head is more shallow.

17 Claims, 4 Drawing Figures

ENDO PROTHESIS WITH A METAL-CERAMIC UNION

BACKGROUND OF THE INVENTION

1. Field of the Invention

The invention relates to an endoprosthesis, particularly a hip joint prosthesis, comprised of a metal shaft for being fitted into the bone and a ceramic head with a matching bore for receiving the free spigot of the metal shaft.

2. Description of the Prior Art

An endoprosthesis of this type is known, for example, from German Laid Open Specification No. 25 48 077. In the joint endoprosthesis described therein, the union between the metal shaft and the ceramic head is made in such a way that the free spigot of the metal shaft is shaped as a male cone while the bore in the ceramic head is shaped as a tapered conical socket. This produces a purely force locking connection when the two parts are pressed directly together. In order to enable use of relatively small cone angles to obtain a reliable friction connection, on the one hand and, on the other hand, to avoid the risk of cracking the ceramic head during heating of the endoprothesis for sterilization, that specification suggests providing grooves of minute profile depth on the male cone and/or in the tapered socket to produce deformation spaces between the metal shaft and the ceramic head into which the metal shaft can elastically expand. In this manner, the contact pressure in the socket of the ceramic head is intended to remain within certain tolerance limits to avoid the risk of cracking the inelastic ceramic head. It has been found, however, that this known technique of making a union by means of a self locking cone is still not sufficiently reliable for attaching a bio-ceramic hip joint head to the metal shaft, and it is particularly not reliable if the union is subjected to alternating loads.

From German Laid Open Specification No. 23 18 396 it is known to unite the metal shaft and cermaic head of a bone joint endoprosthesis by a screw connection. However, for reasons of cost of manufacture and for reasons of strength, a sufficiently fine thread for screwing inside the ceramic head cannot be used. Therefore, it has been suggested to insert a threaded metal sleeve into the ceramic head and to secure it in the head as an intermediate member between the ceramic head and the metal shaft. This made it possible to use a fine thread between the threaded sleeve and the metal shaft. But, there still were serious problems in securing the threaded sleeve inside the ceramic head. Furthermore, it proved necessary to provide additional constructional means to secure the screw connection. The use of an intermediate member between the metal shaft and the ceramic head and the need to secure the screw connection made the arrangement of this endoprosthesis so complicated that the idea of using a screw connection between a ceramic head and a metal shaft was again abandoned.

SUMMARY OF THE INVENTION

It is the object of the present invention to produce a bone joint endoprothesis in which the union between the metal shaft and the ceramic head is secure against loosening under alternating loads and under temperature changes.

It is another object of the invention to prevent overloading of the ceramic head.

It is yet another object of the invention to provide an effective screw connection, rather than a plug connection, between the ceramic head and the metal shaft.

It is a further object of the invention to design such a union in a simple way.

According to the invention, the union between the metal shaft and the ceramic head of the endoprosthesis is a screw connection. This connection comprises a round internal thread inside the ceramic head. The turns or loops of this thread define an approximately sinusoidal profile moving longitudinally along the head. The connection is further comprised of an external thread on the spigot of the metal shaft. Each turn or loop of the spigot thread has a rounded periphery which mates with the grooves in the thread in the ceramic head. The spigot thread has flat, preferably parallel, deep side walls, making this thread a flat thread. In the spigot thread, the profile height or thread depth h of the thread is greater than the profile width or longitudinal length b along the spigot of each loop of the thread.

In an endoprosthesis, a screw connection is superior to a plug connection. According to the invention, high security against loosening of the screw connection is achieved during tightening of the screw connection by elastic deformation of the flat sides of the thread of the metal spigot, particularly as these sides extend far beyond a relatively small thread base. This results in a uniform distribution of the clamping force produced along the line of contact of the thread and a hysteresis effect which may be compared with that of a cup spring or Belleville washer. Secondly, a high initial stress in the screw connection, and thus a high security against loosening during alternating loading on the endoprosthesis, can be obtained without overloading of the ceramic head. Further security against loosening of the screw connection is given by the high friction between the metal and ceramic surfaces along the sides of the threads on the metal spigot and in the ceramic head. The complete endoprosthesis is comprised of a ceramic head and a metal shaft.

The risk of overloading the ceramic head while it is being heated for being sterilized is avoided because the different shapes of the threads on the threaded spigot and in the threaded bore provide sufficient play, of up to several tenths of millimeters, in the event of enlargement of the threaded spigot due to thermal expansion. Because an endoprosthesis constructed according to the invention is so insensitive to heating, it can be exposed, without any danger, to high-temperature sterilization at over 250° C. This insensitivity of the joint to thermal expansion has the further advantage that the choice of metal alloys for the metal shaft is not restricted to alloys which have a thermal coefficient of expansion corresponding to that of the ceramic material used. Thus, in addition to desirable, but expensive, titanium or titanium alloys for example, chrome-cobalt steels or other chrome steel alloys can be used for the metal shaft.

In a preferred embodiment of the invention, the ratio $h/b$ of profile height $h$ and profile width $b$ of the external thread of the spigot shall not be less than 2. For other combinations of material and other dimensions of components, other values for the ratio $h/b$ may apply.

In further development of the invention, the first loop or turn of the thread on the metal spigot is of a smaller width than the other turns of the thread. Then before the ceramic head touches the outer collar of the metal shaft, the first turn of the thread can touch a shoulder-like rim at the end of the thread in the ceramic head. On tightening of the screw connection, the first turn of the thread will be plastically deformed, i.e. squashed, and this provides additional security against loosening of the screw connection.

The invention further relates to a process for securing the screw connection of a threaded metal spigot with a flat thread and a ceramic head with an internal thread of approximately sinusoidal profile, in which the metal shaft has been heated to a temperature of about 250° C. before screwing into the ceramic head. On being heated, the metal shaft expands along its longitudinal direction. The ceramic head can then be tightened on the metal shaft, using a normal torque force for tightening and this torque force is limited by the highly polished spherical surface of the sphere of the ceramic head. The tight fit of the screw connection is strengthened by an increase in the axial screw force which results from contraction of the shaft during cooling. In this way, the torque required for loosening of the screw connection is significantly greater than the torque that can be applied during tightening because the highly polished spherical surface of the ceramic head limits tightening, and is greater than the torque which would be required if an external many sided rim were used. For example, with a sphere of 32 mm diameter and a normal tightening torque of about 3,000 N × cm and a heating temperature of about 250° C., the torque required for loosening of the screw connection is in excess of 4,000 N × cm i.e. beyond the limit given by the friction contact at the surface of the sphere. At room temperature, a sphere which has been tightened in this way can be loosened only if the surface of the sphere is roughened, i.e. if the frictional contact is improved.

Since heating of the threaded spigot produces expansion in both the longitudinal and the transverse directions, it can be advantageous to shape the sides of the thread in the ceramic head differently. The load bearing side of each thread in the ceramic head would be slightly flatter than the opposite free side of that thread. The sliding off of the individual metallic threads, which results from their contraction in the radial direction, can be reduced by making the side of the metallic profile more flat, whereby the magnitude of the screw force that is produced in the axial direction is increased.

Although the screw connection according to the invention is particularly suitable for uniting a ceramic head and a metal shaft for an endoprosthesis, such a screw connection generally can be advantageously used for joining any other ceramic component and metal component.

BRIEF DESCRIPTION OF THE DRAWINGS

Other objects and features of the invention may be understood from the following description taken with reference to the accompanying drawings, wherein:

FIG. 1a is an enlarged view of a fragment of the prosthesis of FIG. 1 showing the internal and external threads on the head and spigot;

DESCRIPTION OF THE PREFERRED EMBODIMENT

Figure 1:
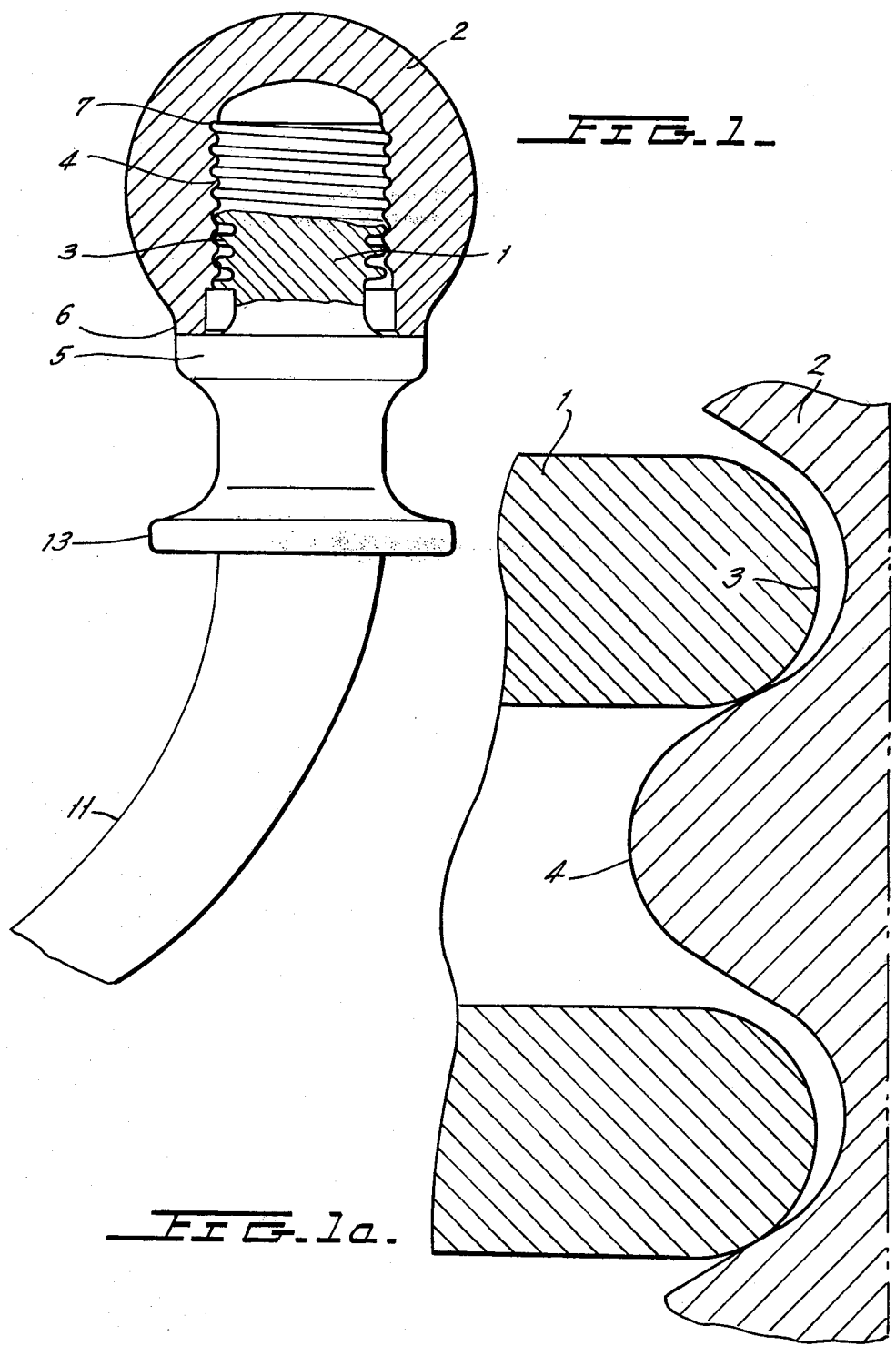
FIG. 1 is a cross-sectional view through a hip joint prosthesis, without the socket of the joint.
Figure 3:
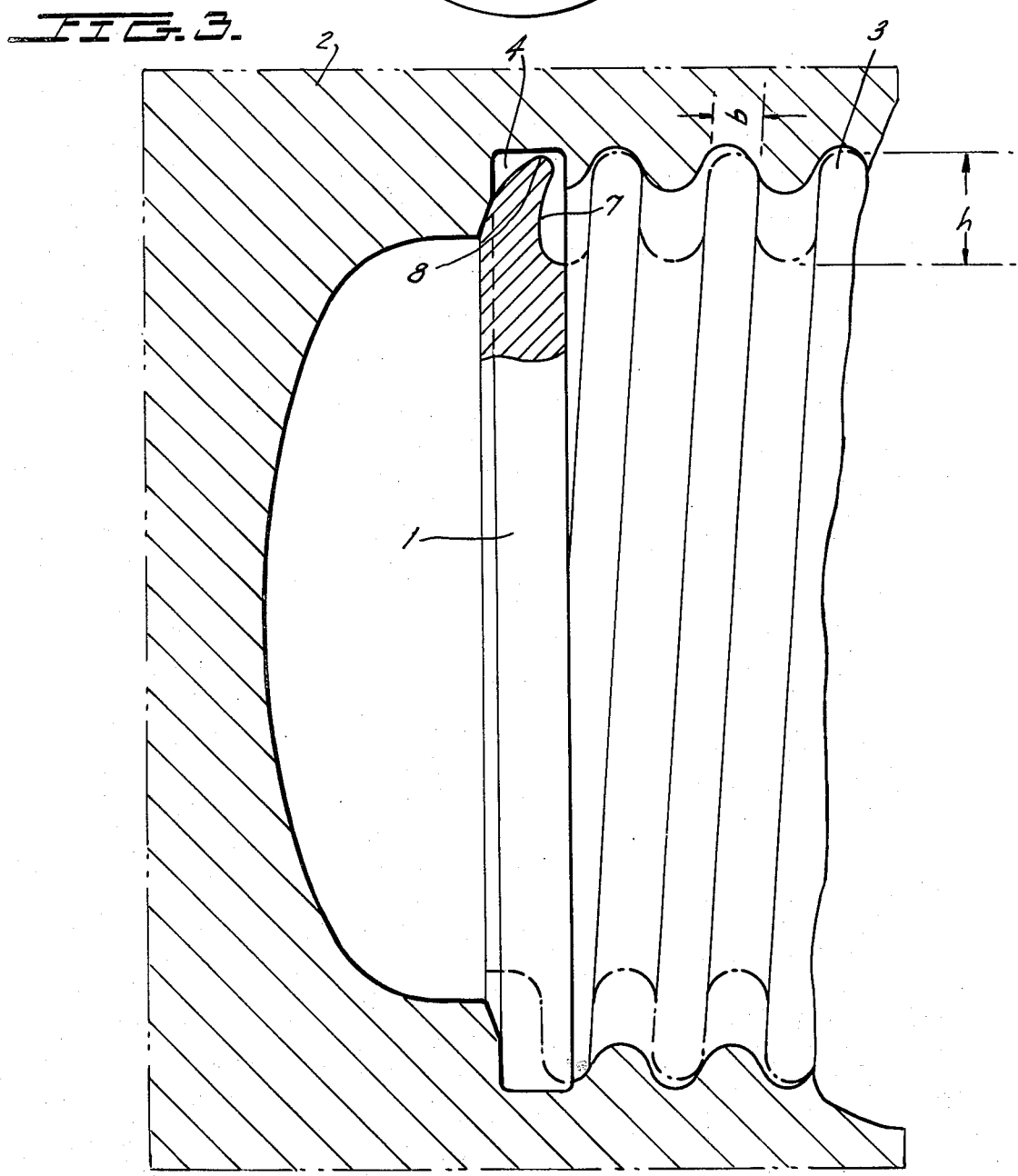
FIG. 3 is an enlarged section of a fragment of the prosthesis particularly showing the first turn of the thread of the metal spigot.

The endoprosthesis according to the invention comprises a metal shaft 11 that is driven into the femur far enough so that a collar 13 around the metal shaft 11 rests against the femur bone. There is a second stop collar 5 on the metal shaft 11 which is spaced from the first collar 13. Above the collar 5, the shaft 11 has a threaded spigot 1 with an external thread 3 which is in the form of a flat sided hellically wound, multi-turn rib, as shown in FIGS. 1a and 3. The thread 3 of the spigot 1 is called a flat thread because the side walls of each turn or loop of the thread, which sidewalls define the radial width of each turn or loop, are flat as they extend radially inwardly from the periphery of the spigot. In addition, the side walls of each turn or loop of the thread are parallel. The profile height or radial depth of the flat thread is designated as h and the profile width or longitudinal length of each turn of the thread is designated as b. In the exemplary embodiment shown, the ratio h/b of the profile height h to the profile width b is about two.

A spherical exterior ceramic material head 2 is screwed onto the threaded spigot 1. The head 2 has an opening into it which receives the threaded spigot 1. The opening has a threaded sidewall to mate with the spigot exterior. The threads on the spigot and inside the head 2 are so shaped and their turns or loops are so spaced as to be matable. The internal thread 4 in ceramic head 2 is a round thread of approximately sinusoidal profile viewed longitudinally along the head. The ribs of the thread 3 are received in the corresponding grooves of the thread 4. The spacing of the loops or turns of the groove of the thread 4 along the longitudinal length of the ceramic head, i.e. the width of each turn, is the same as the width b for the spigot thread rib, but the depth or profile height of the groove of the thread 4 is less than that dimension h of the rib of the thread 3. To improve the locking between the spigot thread and the ceramic head thread, the load bearing (lower in FIG. 1a and right in FIG. 3) side of the groove of the thread 4 in the head 2 is slightly flatter than the other side of that groove, for increasing the surface contact with the corresponding flat side of the respective turn of the rib like spigot thread 3.

Figure 2:
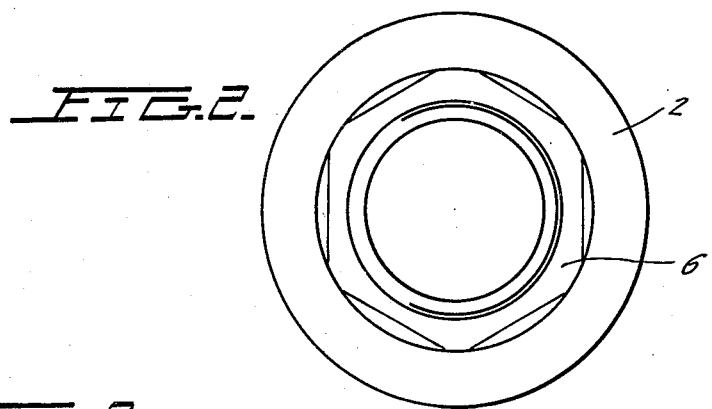
FIG. 2 is a cross-section of the ceramic head of the prosthesis with a many-sided collar.

The lower end of the spherical head 2 terminates in a many sided collar 6 around the threaded opening in the head. A six sided collar 6 is illustrated in FIG. 2. The collar 6 provides means for tightening the screw connection by means of a wrench.

In the mounted state shown in FIG. 3, a section of the ceramic head 2 and the metal spigot 1 are visible. The first turn 7 of the thread of the metal spigot 1 is of smaller width b than the remaining turns 3. It is deformed to have a shoulder-like rim 8 which is located at the end of the internal thread 4 in ceramic head 2. The rim provides additional security against loosening of the screw connection.

Although the present invention has been described in connection with a preferred embodiment thereof, many variations and modifications will now become apparent to those skilled in the art. It is preferred, therefore, that the present invention be limited not by the specific disclosure herein, but only by the appended claims.

What we claim is:

1. A bone joint endoprosthesis comprising:

a metal shaft having a spigot defined thereon; said spigot having an external thread defined thereon; said external thread being comprised of a raised rib extending around said spigot; said external thread rib having a profile height, which is the radial height of said rib on said spigot, and having a profile width, which is the longitudinal length of said rib along said spigot;

a ceramic head having an opening defined therein in which said externally threaded spigot is received; said opening being defined by a side wall which is internally threaded with an internal thread which is mated with said spigot external thread; said internal thread being comprised of a groove into said side wall in said opening and said external thread rib being received in said groove; and said internal thread having a profile height into said side wall which is less than said profile height of said external thread rib.

2. The bone joint endoprosthesis of claim 1, wherein both said internal thread and said external thread are comprised of a plurality of turns around said ceramic head opening sidewall and said spigot exterior, respectively.

3. The bone joint endoprosthesis of claim 2, wherein said rib of said external thread has flat side walls between which said profile width of said external thread rib is defined.

4. The bone joint endoprosthesis of claim 3, wherein said internal thread is generally sinusoidal in profile along the longitudinal length of said ceramic head.

5. The bone joint endoprosthesis of claim 4, wherein said internal thread groove has a load bearing side, which engages the opposed said side of said external thread rib, and said internal thread groove has an opposite free side; said internal thread groove load bearing side being flatter than said internal thread groove free side.

6. The bone joint endoprosthesis of claim 5, wherein said profile height of said external thread rib is greater than said profile width thereof.

7. The bone joint endoprosthesis of claim 2, wherein said head is generally spherical in shape on its exterior.

8. The bone joint endoprosthesis of claim 7, wherein said head has a plural sided collar defined thereon and extending around said opening into said head.

9. The bone joint endoprosthesis of any one of claims 2, 3 or 6, wherein said external thread includes a first said turn toward the free end of said spigot; said first turn being smaller in its said profile width than the remaining said turns of said external thread.

10. The bone joint endoprosthesis of claim 2, wherein said ceramic material of said head is aluminum oxide and said metal shaft is comprised of titanium.

11. The bone joint endoprosthesis of claim 2, wherein said ceramic material of said head is aluminum oxide and said metal shaft is comprised of chromium-cobalt steel.

12. The bone joint endoprosthesis of claim 1, wherein said profile height of said external thread rib is greater than said profile width thereof.

13. The bone joint endoprosthesis of claim 12, wherein said rib of said external thread has flat side walls between which said profile width of said external thread rib is defined.

14. The bone joint endoprosthesis of claim 13, wherein the said flat side walls of said external thread rib are parallel.

15. A method of making a bone joint endoprosthesis, comprising the steps of:
   forming a rib like external thread with flat, generally parallel side walls of the rib, and having a plurality of turns thereof on the exterior of a spigot of a metal shaft;
   forming a mating internal thread comprised of a groove having a plurality of turns in the side wall that defines an opening in a ceramic head;
   forming the profile height, which is the radial height of the external thread rib on the spigot between the side walls, of the external thread to have a greater radial height than the cooperating profile height of the groove of the internal thread in the opening of the ceramic head;
   inserting the spigot into the threaded opening of the ceramic head by matingly screw connecting the spigot into the ceramic head;
   prior to inserting the spigot into the opening in the ceramic head, heating the metal shaft to an elevated temperature.

16. The method of claim 15, wherein the shaft is heated to a temperature of about 250° C.

17. The method of claim 15, wherein the shaft is permitted to be cooled after the spigot is inserted into the opening in the ceramic head.

* * * * *

UNITED STATES PATENT AND TRADEMARK OFFICE
CERTIFICATE OF CORRECTION

PATENT NO. : 4,225,981
DATED : October 7, 1980
INVENTOR(S) : ANTON ZEIBIG

It is certified that error appears in the above-identified patent and that said Letters Patent are hereby corrected as shown below:

Please amend the title of the above identified patent to read:

-- ENDOPROSTHESIS WITH A METAL-CERAMIC UNION --

Signed and Sealed this

Sixth Day of January 1981

[SEAL]

Attest:

SIDNEY A. DIAMOND

Attesting Officer

Commissioner of Patents and Trademarks